United States Patent [19]

Keim et al.

[11] 4,405,815

[45] Sep. 20, 1983

[54] PROCESS FOR THE PRODUCTION OF ACETALDEHYDE AND ETHANOL

[75] Inventors: Karl-Heinz Keim, Heimerzheim; Joachim Korff, Bornheim-Sechtem, both of Fed. Rep. of Germany

[73] Assignee: Union Rheinische Braunkohlen Kraftstoff Aktiengesellschaft, Wesseling, Fed. Rep. of Germany

[21] Appl. No.: 325,812

[22] Filed: Nov. 30, 1981

[30] Foreign Application Priority Data

Dec. 5, 1980 [DE] Fed. Rep. of Germany ....... 3045891

[51] Int. Cl.$^3$ ............................................. C07C 45/49
[52] U.S. Cl. ................... 568/487; 568/902; 568/489
[58] Field of Search ................... 568/487, 902

[56] References Cited

U.S. PATENT DOCUMENTS

| 3,285,948 | 11/1966 | Butter | 568/487 |
| 4,239,704 | 12/1980 | Pretzer et al. | 568/487 |
| 4,239,705 | 12/1980 | Pretzer et al. | 568/487 |
| 4,239,924 | 12/1980 | Pretzer et al. | 568/487 |
| 4,253,987 | 3/1981 | Fiato | 568/902 |
| 4,262,154 | 4/1981 | Gane et al. | 568/487 |
| 4,306,091 | 12/1981 | Gauthier-Lafaye | 568/487 |
| 4,320,230 | 5/1982 | Doyle | 568/487 |
| 4,328,375 | 5/1982 | Barlow | 568/487 |

Primary Examiner—Werren B. Lone
Attorney, Agent, or Firm—Connolly and Hutz

[57] ABSTRACT

Improved process for the production of acetaldehyde and ethanol by reacting methanol with carbon monoxide and hydrogen in the presence of a catalyst system containing cobalt, elemental iodine or bromine as promotor and a polydentate phosphorus, arsenic, antimony or bismuth compound using one or more metals from the group comprising chromium, molybdenum, tungsten, uranium, titanium, vanadium, iron and nickel as co-catalyst.

6 Claims, No Drawings

PROCESS FOR THE PRODUCTION OF ACETALDEHYDE AND ETHANOL

BACKGROUND OF THE INVENTION (1) Field of the Invention

This invention relates to a process for the production of acetaldehyde and ethanol by reacting methanol with hydrogen and carbon monoxide in the presence of a catalyst system which, in addition to cobalt, contains a metal from the group comprising chromium, molybdenum, tungsten, titanium, vanadium, iron, nickel, as well as halogen as promoter and a polydentate ligand.

(2) Description of the Prior Art

Acetaldehyde and ethanol are important organic starting materials. It is known that they can be obtained by the homologisation of methanol. To this end, methanol is reacted with hydrogen and carbonmonoxide at elevated temperature and pressure in the presence of a catalyst system of cobalt, a halogen, preferably iodine, as promoter and a ligand, for example a tertiary monophosphine, the reaction optionally being carried out in a solvent (EPA No. 0,001,937). Methanol conversions of up to 57.7% are obtained for an ethanol selectivity, including the secondary products which can be worked up into ethanol, of 55.8%, in other words the yield of ethanol amounts to 32.2%, based on the methanol used. Recently the mono-ligand has been replaced by socalled polydentate ligands, e.g. ligands containing 2 or more central atoms, for example phosphorus (EPA No. 0,010,373). In this case, too, the reaction is carried out at elevated temperature (150°–250° C.) and pressure (100–300 bars). Synthesis gas obtained by gasifying coal for example is used as the gas containing hydrogen and carbon monoxide. In the absence of a solvent, the yield of ethanol amounts to 32.9% and, in the presence of a solvent, to 36.3%. In this connection, it has also been proposed to introduce a second metal, namely ruthenium, into the catalyst system. This is in line with earlier proposals to add a noble metal, namely ruthenium or osmium, during the homologisation of methanol activated by cobalt, halogen and a monophosphine ligand (U.S. Pat. No. 4,133,966).

Although it has been possible to increase the conversion and selectivity of the homologisation reactions by virtue of the improvements made in recent years to the catalysts used, a further increase in these values is still desirable.

SUMMARY OF THE INVENTION

According to the invention, this object is achieved by a process for the production of acetaldehyde and ethanol by reacting methanol with hydrogen and carbon monoxide at elevated temperature and pressure in the presence of a catalyst system containing cobalt, elemental iodine, bromine, and iodine and/or bromine compound as promoter and a polydenate ligand with phosphorus, arsenic, antimony or bismuth as donor atoms, characterised in that one or more metals from the group comprising chromium, molybdenum, tungsten, uranium, titanium, vanadium, iron, nickel, is introduced into the catalyst system.

The metals used in addition to cobalt may be used in commensurate form, preferably in ionic form, for example as acetyl acetonate, acetate, formate, propionate, iodine, bromide, or in the form of their carbonyls. However, they may also be used for example in finely divided form or applied to a support. The cobalt is used in a quantity of from 0.01 to 1.5% by weight and preferably in a quantity of from 0.02 to 0.5% by weight whilst the second metal is used in a quantity of from 0.01 to 4% by weight and preferably in a quantity of from 0.02 to 2% by weight, based on the methanol used.

It has proved to be of particular advantage to add molybdenum, tungsten, chromium and/or nickel because, in their case the formation of undesirable secondary products is negligible. It can be of advantage to add several metals from the above-mentioned group to the catalyst system. The formation of carbonyl or hydrocarbonyl complexes in the reaction mixture must be guaranteed.

DESCRIPTION OF THE PREFERRED EMBODIMENTS

The reaction is promoted by the usual halogens, for example elemental iodine or bromine or compounds thereof.

Suitable promoters are hydrogen halide, cobalt or alkali halide, alkyl or aryl halide or even phosphonium halides. Mixtures of these compounds may also be used. The iodine or bromine is added in a quantity of from 0.1 to 3% by weight and preferably in a quantity of from 0.2 to 1.5% by weight, based on the methanol used.

The polydentate ligands known for the homologisation of methanol may be used as ligands. It is preferred to use bidentate compounds corresponding to the following formula

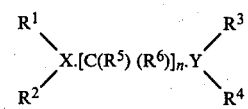

in which the donor atoms X and Y are phosphorus, arsenic, antimony or bismuth and $R^1$, $R^2$, $R^3$ and $R^4$ represent mono-valent organic groups. Although $R^5$ and $R^6$ preferably represent hydrogen atoms, they may also represent mono-valent organic groups. n is a number of from 1 to 8 and preferably from 2 to 6. The groups may for example be straight-chain or branched-chain, preferably saturated hydrocarbon groups containing from 1 to 20 carbon atoms. The groups may be aliphatic or cycloaliphatic or even aromatic in character. The hydrogen atoms may be replaced for example by organic radicals, such as, for example, methyl, ethyl, propyl, isopropyl, dodecyl, cyclohexyl, benzyl, phenyl, p-ethylphenyl. In addition to carbon and hydrogen, the groups may contain for example oxygen, sulfur or halogen. The carbon bridge between the donor atoms may even be cyclic for example and contain heteroatoms or even unsaturated groups. It is also possible for example to use tridentate ligands of which the structure corresponds to that of the bidentate. The ligands may also have a branched structure. The molar ratio of the donor atoms, for example phosphorus, to the second metal amounts to 1:0.1-5 and preferably to 1:1-2.

Monophosphines for example may optionally be used in addition to the polydentate ligands.

The reaction pressure should be in the range from 100 to 450 bars, advantageously in the range from 230 to 400 bars and, more particularly, in the range from 250 to 350 bars. The reaction temperature is in the range from about 150° to 390° C. and advantageously in the range from 180° to 210° C. The residence times are generally between 5 and 120 minutes.

The ratio of hydrogen to carbon monoxide is advantageously of the order of 1:1, although it may be varied within wide limits, for example from 4:1 to 1:4. Since the presence of small inert fractions, such as $CO_2$, $N_2$, $CH_4$, does not affect the reaction, synthesis gas of any of the standard qualities may be used. The process may be carried out either continuously or in batches. The products are worked up in the usual way, for example by distillation or extraction.

If desired, the reaction may be carried out in the presence of additives such as, for example, organic acids and acid derivatives, such as acetic acid, methyl acetate, benzoic acid, aryl halides, such as chlorobenzene, ethers, such as diphenyl ether, alcohols and ketones, such as n-propanol, acetone, also apolar solvents, such as alkanes, benzene and alkyl-substituted benzenes.

The known addition of noble metals acting as hydrogenation catalysts, particularly ruthenium or osmium, or for example of iridium can also be of advantage in the case of the catalyst system according to the invention. These metals may be applied for example to supports, such as aluminium oxide, or used in the form of carbonyls or hydrocarbonyls. In addition to the homologisation reaction, the hydrogenation of acetaldehyde or acetal takes place to a significant extent, so that it is possible to control the ratio of acetaldehyde to ethanol within wide limits.

The addition according to the invention of one or more of the above mentioned metals to the catalyst system provides for an increase in the conversion and selectivity of the homologisation reaction by comparison with the use of cobalt on its own.

EXAMPLE

In the tests, quantities of 50 ml of methanol, to which 160 mg of Co (acetate)$_2$.4H$_2$O had been added, were reacted after the addition of the second metal compounds, aqueous hydrogen iodide solution (57%) and a ligand, at 200°–210° C. and 275–295 bars in the presence of a gas mixture of carbon monoxide and hydrogen (ratio by volume 1:1). The reactions were carried out in an autoclave of Hastelloy C. The reaction time was of the order of 1 hour, unless otherwise indicated. The metals tungsten and molybdenum were used in the form of hexacarbonyls, chromium, vanadium and iron in the form of triacetyl acetonates, titanium in the form of diacetyl acetonate and nickel and uranium in the form of acetates. Ruthenium was applied as ruthenium metal to $Al_2O_3$. The following ligands were used:

A bis-(diphenylphosphino)-ethane
A bis-(diphenylphosphino)-butane
C bis-(diphenylarsino)-butane.

The test conditions and results are set out in the following Tables. In each case, the selectivity quoted includes the acetaldehyde/ethanol initial products.

TABLE 1

| Test No. | Second metal, mg | | HI-solution mg | Ligand mg |
|---|---|---|---|---|
| 1 | tungsten | 675 | 286 | A 510 |
| 2 | " | 675 | 572 | A 510 |
| 3 | " | 225 | 286 | A 510 |
| 4 | molybdenum | 338 | 286 | A 255 |
| 5 | " | 338 | 286 | C 385 |
| 6 | chromium | 225 | 429 | A 255 |
| 7 | " | 450 | 429 | B 270 |
| 8 | nickel | 319 | 286 | B 270 |
| 9 | vanadium | 223 | 429 | A 255 |
| 10 | " | 446 | 429 | A 255 |
| 11 | iron | 270 | 286 | A 255 |
| 12 | titanium | 168 | 286 | A 255 |
| 13 | uranium | 276 | 429 | A 255 |
| 14 | molybdenum/ruthenium | 169/75 | 429 | A 255 |

TABLE 2

| Test No. | Conversion, % by weight (based on the methanol used) | Selectivity, % acetaldehyde + ethanol |
|---|---|---|
| 1 | 68.2 | 87.7 |
| 2 | 80.4 | 69.2 |
| 3 | 65.1 | 89.5 |
| 4 | 73.0 | 77.5 |
| 5 | 73.4 | 72.2 |
| 6 | 78.5 | 77.0 |
| 7 | 76.9 | 65.3 |
| 8 | 73.0 | 69.1 |
| 9 | 76.3 | 67.4 |
| 10 | 75.8 | 61.2 |
| 11 | 62.8 | 82.9 |
| 12 | 73.2 | 64.6 |
| 13 | 70.6 | 59.1 |
| 14 | 59.8 | 63.7 |

What we claim is:

1. In a process for the production of acetaldehyde and ethanol by reacting methanol with hydrogen and carbonmonoxide at elevated temperature and pressure in the presence of a catalyst system containing cobalt, and a promoter selected from the group consisting of iodine, bromine, an iodine compound and a bromine compound and one or more polydentate ligands with donor atoms of the group consisting of phosphorus, arsenic, antimony and bismuth, the improvement which comprises additionally introducing into the catalyst system one or more metals from the group consisting of chromium, molybdenum, tungsten, uranium, titanium, vanadium, iron and nickel.

2. A process as claimed in claim 1 wherein one or more metals of the group consisting of molybdenum, tungsten and chromium are additionally introduced into the catalyst system.

3. A process as claimed in claim 1 wherein nickel is introduced into the catalyst system.

4. A process as claimed in claim 1 wherein one or more metals of the group consisting of ruthenium, osmium and iridium are additionally introduced into the catalyst system.

5. A process as claimed in claim 1 wherein hydrogen iodide and hydrogen bromide are used as promoter.

6. A process as claimed in claim 1 wherein bis-phosphines are used as ligands.

* * * * *